(12) United States Patent
Wäckers et al.

(10) Patent No.: US 9,992,982 B2
(45) Date of Patent: Jun. 12, 2018

(54) MITE REARING METHODS

(71) Applicant: BIOBEST BELGIUM N.V., Westerlo (BE)

(72) Inventors: Felix Wäckers, Antwerpen (BE); Arijs Yves, Westerlo (BE)

(73) Assignee: Biobest Belgium N.V., Westerlo (BE)

( * ) Notice: Subject to any disclaimer, the term of this patent is extended or adjusted under 35 U.S.C. 154(b) by 197 days.

(21) Appl. No.: 14/764,591

(22) PCT Filed: Feb. 7, 2014

(86) PCT No.: PCT/EP2014/052382
§ 371 (c)(1),
(2) Date: Jul. 30, 2015

(87) PCT Pub. No.: WO2014/122242
PCT Pub. Date: Aug. 14, 2014

(65) Prior Publication Data
US 2015/0366177 A1    Dec. 24, 2015

(30) Foreign Application Priority Data
Feb. 7, 2013  (EP) .................................. 13154327

(51) Int. Cl.
*A01K 67/00*    (2006.01)
*A01K 67/033*   (2006.01)

(52) U.S. Cl.
CPC .................. *A01K 67/033* (2013.01)

(58) Field of Classification Search
CPC ............... A01K 67/00; A01K 67/033
USPC .................... 119/6.5; 426/2; 800/8
See application file for complete search history.

(56) References Cited

U.S. PATENT DOCUMENTS

| 6,129,935 A * | 10/2000 | White ................ A23K 50/90 119/6.5 |
| 2009/0012186 A1 | 1/2009 | Blockmans et al. |
| 2009/0205057 A1 | 8/2009 | Blockmans et al. |
| 2010/0119645 A1 * | 5/2010 | Fidgett ................ A01N 63/00 426/2 |

FOREIGN PATENT DOCUMENTS

| GB | 2 393 890 A | 4/2004 | |
| JP | 2007297293 A * | 11/2007 | |
| WO | WO 2003086067 A1 * | 10/2003 | ........... A01G 67/033 |
| WO | 2006057552 A1 | 6/2006 | |
| WO | 2007075081 A1 | 7/2007 | |

OTHER PUBLICATIONS

M.Nomikou et al., Phytoseiid predators of whiteflies feed and reproduce on non-prey food sources, 2003, Population Biology, University of Amsterdam, P.O. Box 94084, 1090 GB Amsterdam, The Netherlands.*
PCT International Search Report and Written Opinion dated Mar. 31, 2014 for PCT Application No. PCT/EP2014/052382, 7 pages.

* cited by examiner

Primary Examiner — David J Parsley
Assistant Examiner — Danielle A Clerkley
(74) Attorney, Agent, or Firm — Amster, Rothstein & Ebenstein LLP

(57) ABSTRACT

The present invention relates to methods for rearing, storing or shipping predatory mites. The methods comprise contacting a rearing population of predatory mites with a succulent plant or one or more parts thereof; and optionally a nutritional source for said predatory mites.

18 Claims, No Drawings

MITE REARING METHODS

CROSS-REFERENCE TO RELATED APPLICATIONS

This application is a U.S. national stage entry under 35 U.S.C. § 371 of PCT International Patent Application No. PCT/EP2014/052382, filed Feb. 7, 2014, which claims priority to European Patent Application No. 13154327.4, filed Feb. 7, 2013, the contents of all of which are incorporated herein by reference in their entirety.

FIELD OF THE INVENTION

Provided herein are methods for rearing, storing or shipping mites such as predatory mites, which can be used in different applications such as for controlling crop pests.

BACKGROUND OF THE INVENTION

Plant pests such as *thrips*, spider mites and whitefly cause considerable damage to various crops such as salad vegetables, cut flowers and ornamental plants, resulting in significant economic loss to growers and higher prices for consumers. Although plant pests may be controlled using chemical pesticides, this is not always possible or desirable. Indeed, the widespread use of chemical pesticides can result in health and environmental problems, and in the appearance of resistant insect varieties.

Alternative methods for plant pest control have been developed, such as the use of natural predators of plant pests. In particular, beneficial insects such as predatory mites are often used in agriculture for biological control of crop pests such as *thrips* or spider mites. The predatory mites may be applied to the plants manually, via controlled release systems, or via other methods.

Predatory mites also have applications in areas of pest control other than crop protection, such as in the protection of animals, animal products or fabrics/carpets.

Predatory mites are typically reared in mass-rearing systems, wherein the mites are provided with food sources such as spider mites, pollen, insect eggs, or artificial diet compositions. The choice of food source typically depends on the mite species to be reared. For example, *Iphiseius degenerans* may be mass-reared on castor bean plants (*Ricinus communis* L.), which provides a continuous supply of pollen on which the mites can develop large populations. Other predatory mites, such as *Amblyseius cucumeris* are easier to rear in large quantities, but are less efficient for *thrips* control.

Especially when mites need to be reared on growing plants this increases costs substantially. Therefore, the use of such predatory mites still is relatively expensive compared to the use of chemical pesticides.

SUMMARY OF THE INVENTION

Described herein are methods for rearing, storing, shipping or introducing mites such as predatory mites, which can be used for controlling pests. The methods are based on the observation that mites can be reared surprisingly well on succulent plants. Accordingly, the present application provides methods for rearing, storing, shipping or introducing mites, characterized in that these methods comprise inoculating the mites on a succulent plant or a part thereof. More particularly, the methods may comprise contacting mites with a succulent plant or a non-reproductive plant part thereof.

In particular embodiments, the methods comprise providing a rearing mite population, a succulent plant or one or more parts thereof, a nutritional source, with or without a carrier material for said mites and allowing said rearing population to feed on said nutritional source.

Different types of nutritional sources are envisaged in the methods described herein. In particular embodiments of the methods envisaged herein, the nutritional source comprises plant pollen. The pollen may be obtained from the same or another succulent plant, but may also be from a non-succulent plant. In certain embodiments, the pollen may be obtained from one or more plant species other than the succulent plant on which the mites are inoculated.

The methods are envisaged to be suitable for different types of mites. In particular embodiments, the mite is a predatory mite. In further particular embodiments, the predatory mites comprise members of the family Phytoseiidae. In further embodiments, the predatory mites are all members of the family Phytoseiidae. More particularly, the methods are envisaged for rearing predatory mites from a genus selected from the group consisting of *Euseius, Amblyseius, Neoseiulus, Iphiseius, Indoseiulus, Kampimodromus,* and *Typhlodromus*. Most particularly the methods envisaged herein utilize plants from plant families selected from the list consisting of Crassulaceae, Cactaceae, and Apocynaceae, or combinations thereof.

Different parts of the succulent plant can be used for rearing, storing, shipping or introducing the mites as envisaged herein. In particular embodiments, the succulent plant leaves are used.

It can be envisaged in the methods provided herein to provide an additional oviposition substrate for the mites.

Also provided herein are compositions, comprising a succulent plant or one or more non-reproductive parts thereof, and a nutritional source for mites.

Also provided herein are compositions, comprising a succulent plant or one or more non-reproductive parts thereof and a population of mites, such as a population of predatory mites. In addition, these compositions may optionally further comprise a nutritional source for the mites and/or a water source. In particular embodiments of these compositions, the nutritional source comprises plant pollen and/or a sugar source.

These compositions are envisaged for use in the rearing, storage, shipment of mites and the introduction of predatory mites. This is of interest in the rearing of predatory mites for use in controlling pests, such as for controlling a crop pest, such as *thrips*, spider mites, whitefly, and the like.

Also provided herein are mite populations, such as predatory mite populations reared by the methods described herein.

The independent and dependent claims set out particular embodiments envisaged herein. Features from the dependent claims may be combined with features of the independent or other dependent claims as appropriate.

The above and other characteristics, features and advantages of the concepts described herein will become apparent from the following detailed description, which illustrates, by way of example, the principles of the invention.

DETAILED DESCRIPTION OF THE INVENTION

While potentially serving as a guide for understanding, any reference signs in the claims shall not be construed as limiting the scope thereof.

As used herein, the singular forms "a", "an", and "the" include both singular and plural referents unless the context clearly dictates otherwise.

The terms "comprising", "comprises" and "comprised of" as used herein are synonymous with "including", "includes" or "containing", "contains", and are inclusive or open-ended and do not exclude additional, non-recited members, elements or method steps. The terms "comprising", "comprises" and "comprised of" when referring to recited components, elements or method steps also include embodiments which "consist of" said recited components, elements or method steps.

Furthermore, the terms first, second, third and the like in the description and in the claims, are used for distinguishing between similar elements and not necessarily for describing a sequential or chronological order, unless specified. It is to be understood that the terms so used are interchangeable under appropriate circumstances and that the embodiments described herein are capable of operation in other sequences than described or illustrated herein.

The values as used herein when referring to a measurable value such as a parameter, an amount, a temporal duration, and the like, is meant to encompass variations of +/−10% or less, preferably +/−5% or less, more preferably +/−1% or less, and still more preferably +/−0.1% or less of and from the specified value, insofar such variations are appropriate to ensure one or more of the technical effects envisaged herein. It is to be understood that each value as used herein is itself also specifically, and preferably, disclosed.

The recitation of numerical ranges by endpoints includes all numbers and fractions subsumed within the respective ranges, as well as the recited endpoints.

All documents cited in the present specification are hereby incorporated by reference in their entirety.

Unless otherwise defined, all terms used in disclosing the concepts described herein, including technical and scientific terms, have the meaning as commonly understood by one of ordinary skill in the art. By means of further guidance, definitions for the terms used in the description are included to better appreciate the teaching of the present disclosure. The terms or definitions used herein are provided solely to aid in the understanding of the teachings provided herein.

Reference throughout this specification to "one embodiment" or "an embodiment" means that a particular feature, structure or characteristic described in connection with the embodiment is included in at least one embodiment envisaged herein. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are also envisaged herein, and form different embodiments, as would be understood by those in the art. For example, in the appended claims, any of the features of the claimed embodiments can be used in any combination.

Described herein are methods for rearing, storing, shipping or introducing mites such as predatory mites, based on the surprising observation that succulent plants and parts thereof are particularly useful to this end. Accordingly, provided herein are methods for rearing, storing, shipping mites and for introducing predatory mites, which comprise contacting a mite population with a succulent plant or a plant part thereof. In particular embodiments, the methods involve inoculating a succulent plant or part thereof with a mite population.

The term "introducing" as used herein in the context of introducing predatory mites, refers to the introduction of predatory mites on or near a crop, organism or item to be protected from pests.

The term "succulent plant" as used herein refers to a plant with thick, fleshy and swollen stems, leaves and/or roots, adapted to dry environments. Succulent plants are also known as "succulents" or "fat plants". As used herein, the term "succulent plant" also includes cacti (family Cactaceae). Non-limiting examples of succulent plants are most members of the families Crassulaceae, Cactaceae, Apocynaceae, Agavaceae, and Aizoaceae. In certain embodiments, the succulent plant is a member of a family selected from the list consisting of Crassulaceae, Cactaceae, Apocynaceae, Agavaceae, and Aizoaceae. In further preferred embodiments, the succulent plant is a member of a family selected from the list consisting of Crassulaceae, Cactaceae, and Apocynaceae. In particular embodiments, for practical purposes, the succulent plant is not a cactus.

It has been found that succulent plants and parts thereof are particularly suitable as host plant material for the mass-rearing of mites, more particularly for the mass-rearing of predatory mites. These plants further are found highly suitable for shipping, storing, of mites and/or introducing predatory mites. It is noted that succulent plants typically are low-maintenance plants which are highly resistant to dehydration, such that in some embodiments, the methods envisaged herein will also result in a significant reduction of rearing cost.

The succulent plant may be used in its entirety. In particular embodiments, only part of the plant is used. It will be understood that as host or rearing material, typically larger parts of the plant are envisaged, such as the leaves, stems or roots. More particularly, the plant part envisaged for rearing is not a reproductive plant part, more particularly not a pollen-bearing plant part, most particularly not pollen. Indeed, as detailed below, the pollen of the succulent plant may be used as a food source, but the methods as envisaged herein particularly relate to the use of the entire plant or a plant part other than pollen as a rearing substrate. The succulent plant parts used in the methods described herein are typically succulent leaves, succulent stems, and/or succulent roots. It was found that the succulent plants or plant parts providing the best results are typically those plants of which the succulent leaves (and/or succulent stem and/or succulent roots) are relatively soft, and wherein the wax layer provided on the succulent leaves (and/or succulent stem) is relatively thin.

The methods, compositions and devices envisaged herein are characterized in that they involve or are adapted for contacting of one or more individuals of a mite population with a succulent plant or a part thereof. In particular embodiments, this implies that no other plants or plant parts more particularly no other non-reproductive or unprocessed plant parts (from other non-succulent plants) are required or used. This can be of interest for methods wherein the use of traditional plants or plant parts is not practical. However, it will be understood that combinations with other plant species can be envisaged and that for certain embodiments the methods envisaged herein will imply the use of non-succulent plants or plant parts.

In particular embodiments, the methods described herein involve rearing, shipping and/or storing the mites on a succulent plant part, for example on succulent leaves. While it is envisaged that the plant part can be provided as sliced or chopped pieces, particular embodiments envisage the use of whole plant parts such as whole leaves, stems or roots.

In a particular embodiment, the succulent plant part is a plant leaf.

In contrast with other leaves, succulent leaves typically dry out more slowly. In particular embodiments envisaged herein, the methods of rearing or storing mites as described herein are characterized in that the plant material need not be or is not replaced within 7, 10, 14, 21 days or longer.

The amount of plant material used in the methods envisaged herein typically depends on the plant species and predatory mite species. Typically, an initial amount (prior to increase of the mite population) of plant material taking into account a surface of about 1 mm$^2$ and 1 cm$^2$ per mite is suitable.

The methods for rearing described herein, also referred to as "rearing methods" are envisaged to be useful in the rearing of mites and are of particular interest in the rearing of predatory mites. It will be understood that this implies that, as starting material, a population of mites is used which is a rearing population. The term "rearing" as used herein broadly refers to breeding, reproducing, surviving and growing of the mites, and includes the propagation and increase of population by means of sexual reproduction. Thus, in essence, a rearing population is capable of increasing the number of its individuals by means of sexual reproduction. Accordingly, the rearing population envisaged for use herein may comprise sexually mature adults from both sexes, and/or individuals of both sexes of immature life stages (such as eggs and/or nymphs) which can mature to sexually mature adults. Additionally or alternatively, the rearing population may comprise one or more fertilized females.

Accordingly, provided herein are methods for rearing a population of a mite species comprising providing a composition (as described herein below) or environment comprising a succulent plant or a plant part thereof and allowing the individuals of the mite population to grow on said composition or in said environment.

Additionally or alternatively, for actions which involve the handling and/or use of mites, such as shipping, storing of mites and/or introducing predatory mites, the use of a substrate for the mites is often required/beneficial. Thus envisaged herein are methods of handling mites, which include the step of contacting a mite population with a composition or environment as described herein comprising succulent plant or a plant part thereof and allowing individuals of the mite population to contact said succulent plant or plant part thereof. In particular embodiments, the methods will facilitate or improve further steps in the handling of the mite population such as the shipping, storing or introducing of said mite population.

The methods described herein are suitable for the rearing, storage, shipment and/or introduction of mites, and envisaged to be particularly useful for the rearing, storage, shipment and/or introduction of phytoseiid predatory mites, i.e. members of the family Phytoseiidae. Phytoseiid predatory mites are widely used for biological control of pests such as spider mites, *thrips*, and whitefly, particularly in greenhouse crops. However, the methods envisaged herein are in no way limited by the envisaged application of the mites and other applications thereof may be envisaged. In particular embodiments, the predatory mites comprise members of the family Phytoseiidae.

Some mite species are known to require plant material for the rearing thereof. The methods described herein are particularly suitable for the rearing of such mite species. However, the present methods can also be used for rearing of other mite species, for which the presence of plant material is not essential.

In certain embodiments, the predatory mites are from a genus selected from the group consisting of *Euseius, Amblyseius, Neoseiulus, Iphiseius, Indoseiulus, Kampimodromus, —Typhlodromalus, Phytoseius* and *Typhlodromus*. These mites are typically generalist mites which can be reared using pollen as food source, and can be reared particularly well by the rearing methods described herein. In particular embodiments, the predatory mites are from the genus *Euseius*.

Non-limiting examples of mite species suitable for use in the presently disclosed rearing methods include *Euseius stipulatus, Amblyseius cucumeris, Typhlodromus pyri, Amblyseius swirskii,* and *Iphiseius degenerans*.

The methods described herein typically comprise inoculating the succulent plant or plant part with a rearing population of mites. In order for the mite population to be sustained, a food source and/or an additional water source may also be required. In particular embodiments, where the mite of interest is a predatory mite, the methods envisaged herein thus comprise providing a prey or non-prey nutritional source for predatory mites. Predatory mites may be reared on various nutritional sources, including pollen, a (factitious) population of a prey such as spider mites or other prey mites, insect eggs, and/or artificial diets. Examples of the rearing of predatory mites on factitious populations of prey are described in GB2393890, EP 2124573, and EP 2380436. Examples of artificial diets are described in U.S. Pat. No. 6,291,007 and WO 2011/010308.

In particular embodiments, the nutritional source is or comprises a sugar source. Preferably, the sugar source may comprise one or more sugars or sugar alcohols selected from sucrose, fructose, glucose, maltose, trehalose, galactose, raffinose, mannitol, sorbitol. Optionally, the sugar source may comprise one or more additives such as a viscosity increasing agent (texturizer) and/or a humectant (water retaining agent). In particular embodiments, the sugar source comprises at least 5 weight % of sugar(s). The sugars may be provided as such or as a composition. The sugar source may be provided in a solid form, or as a liquid such as an aqueous solution or a syrup.

The rearing, storing, shipping or introduction of mites on or making use of succulent plant (parts) can be particularly successful when the nutritional source is or comprises pollen. Many predatory mite species are known to be able to establish and maintain on a supply of pollen in the absence of prey species.

In particular embodiments of the methods described herein it may be envisaged that the succulent plant provides a source of pollen. However, where the succulent plant does not provide a continuous supply of pollen or where the use of only non-pollen bearing plant parts of the succulent plant is envisaged, the pollen can be provided artificially. The choice of pollen is not restricted by the type of succulent plants used in the rearing method. In particular embodiments, it is envisaged that the pollen is obtained from one or more plant types other than that of the succulent plant used as a host. In particular embodiments, the pollen is from a non-succulent plant.

Many plants are known to provide pollen on which mites and more particularly predatory mites can feed. In particular embodiments, the pollen are pollen from cattail (genus *Typha*), as these pollen are relatively insensitive to humidity. Other suitable pollen include, but are not limited to cherry, apricot, walnut, hazel, birch, apple, pear, plum, almond, maize, *Hirschfeldia incana, Mesembryanthenum, Ricinus communis, Malephora crocea,* and *Brevipalpus chilensis* pollen.

In particular embodiments, the pollen may be fresh. In certain embodiments, the pollen may be treated before they are used as a nutritional source for the mites. More particularly, the pollen may be frozen and/or sterilized, for example via a treatment with UV irradiation.

The pollen or other food source may be made accessible to the rearing population by applying it to the succulent plant (parts). Additionally or alternatively, the food source may be provided on the carrier (see further). Where the food source is pollen, application of pollen may be performed by dusting the pollen on the plant (parts). In certain embodiments, the pollen is provided via a pollen applicator, for example as described in US 2011/0162266. In the rearing methods described herein, the pollen is typically provided regularly, preferably at a frequency ranging from once per day to once per fortnight. In particular embodiments, the pollen is provided once per week. The amount of pollen to be added may depend on the pollen type and the predatory mite species. In general, an amount ranging between 0.01 g and 1 g per 1000 mites per week is sufficient. In particular embodiments, between 0.01 g and 0.5 g of pollen are added per 1000 mites and per week, for example about 0.05 g or about 0.1 g per 1000 mites and per week.

The method of applying the nutritional source to the mite is not critical. In the methods envisaged herein, the nutritional source is provided to the rearing population in such a way that the rearing population is further allowed to feed on the nutritional source. This will be explained more in detail herein below.

In particular embodiments, methods for rearing, shipping, storing or introducing mites are provided which are characterized in that they comprise inoculating a rearing population of mites on a succulent plant or one or more parts thereof; and providing a nutritional source for said mites.

In particular embodiments, the methods envisaged herein comprise rearing, shipping or storing the mites on a carrier. The carrier may be any particulate material which is suitable to provide a carrier surface to the mite individuals and/or the host plant and nutritional source as envisaged herein. Examples of suitable carriers are light granular materials such as (wheat) bran, buckwheat husks, rice husks, saw dust, wood chips, corn cob grits, vermiculite, and the like.

The carrier may facilitate accommodating the mites during the rearing, storing and shipping, and/or may facilitate the subsequent collection of the mites and/or their introduction to a site of interest, such as a crop. In particular embodiments, as soon as the rearing population is large enough, some or all of the carrier (comprising mites) may be collected and this may as such be distributed for application, such as onto a crop plant.

In order to further the rearing of the mites in the methods envisaged herein, it may be of interest to provide an oviposition substrate for the female mites. Thus, in particular embodiments, the methods described herein further comprise bringing the rearing mite population into contact with a (dedicated) oviposition substrate. Suitable oviposition substrates for rearing mites that have been described in the art are suitable for use in the context of the present invention. In particular embodiments, the oviposition substrate comprises or consists of fibers or threads such as cotton fibers or threads, or a fibrous material such as a fabric, or any hirsute surface. Further suitable oviposition substrates may include open cell foam materials, preferably comprising openings with a size between 400 and 800 μm. Fibrous carrier substrates or hirsute plants may also provide the oviposition substrate.

The rearing conditions envisaged for the methods described herein typically correspond to the rearing conditions known in the art. More particularly, the rearing population is preferably maintained at 20 to 30° C. and 65 to 90% relative humidity. In particular embodiments, additional measures are provided to ensure the envisaged relative humidity. Thus, in particular embodiments, a (moist) hydrophilic material is provided in the vicinity of the rearing mite population, host plant material and/or carrier to help maintain a moist environment. Suitable hydrophilic materials include, but are not limited to, paper, hydrophilic gels such as polyacrylamide gel, or a fabric such as a cotton fabric.

In the methods envisaged herein, the rearing population and succulent plant (parts), as well as optionally the nutritional source, water source, carrier, oviposition substrate, and hydrophilic material, are typically provided in a single volume, for example a container (also referred to as an arena), incubator, growth room or greenhouse.

In particular embodiments, the methods envisaged herein comprise providing the succulent plant (parts) and rearing population in a container or an arena. In further particular embodiments, the methods involve adding one or more of the following: a nutritional source, a carrier, an oviposition substrate, and a source of water.

The container or arena may be of any type which is suitable for restraining mite individuals. It may be open, or closed. The shape of the container is not critical, and may for example be cuboid, cylindrical, etc. In particular embodiments, the container does not have a fixed shape, and may for example comprise a bag. The material(s) of which the container is made is not critical, and may for example comprise one or more materials selected from a polymer (such as polyethylene, polypropylene, polystyrene, and the like), glass, ceramic, wood, and metal.

If closed, the container or arena may comprise means which facilitate exchange of metabolic gases and heat between its interior and its exterior, such as ventilation holes. To prevent the escape of individuals of the mite population from the container, the ventilation holes may be covered, e.g. with a mesh.

In particular embodiments, the container is adapted to the (controlled) release of mobile stages of the predatory mite in a crop. This is particularly suitable for the introduction of predatory mites. For example, the container may be provided with one or more apertures which can be opened and closed. Additionally, or alternatively, the container may be provided with one or more small apertures, thereby enabling a continuous but controlled release of predatory mites from the container. In particular embodiments, the container is dimensioned such that it can be hung in the crop via a hanging means such as a hook or a cord; or that it can be placed at the basis of the crop.

The present application further provides compositions and devices comprising a succulent plant (or one or more parts thereof) for use in the rearing, storage, shipment or introduction of mites such as predatory mites. More particularly the plant part is a non-pollen bearing plant part. It will be understood to the skilled person that the plant or plant part envisaged in the compositions provided herein is an isolated plant or plant part.

In particular embodiments, the device is a rearing device or shipping device. The device may comprise a container for holding a succulent plant or plant part thereof, and optionally one or more other components as described herein.

In particular embodiments the device is a rearing device comprising an exit for at least one motile life stage of the mite species.

Such compositions or devices may be specifically adapted for use in the rearing, storage, shipment or introduction of mites and may thus include one or more components selected from a nutritional source for mites, a carrier, an oviposition substrate, and a hydrophilic material. In particular embodiments, the composition comprises a food source. However, the compositions need not comprise a food source, as this can be provided separately.

In certain embodiments the compositions or devices comprise pollen as a nutritional source. More particularly, the nutritional source may comprise plant pollen, preferably obtained from another plant type than the one used as the succulent plant or part thereof. In particular embodiments, the compositions or devices comprising a succulent plant or plant part do not comprise pollen on/from said plant.

Such compositions or devices may be used in the methods described herein. In particular embodiments, the devices or compositions envisaged herein comprise a population of predatory mites.

Also provided herein are predatory mite populations obtainable by the rearing methods described herein. Such a mite population may be used in the biological control of plant pests.

Further provided herein is the use of the compositions and/or devices as described above comprising a succulent plant or one or more parts thereof and a population of predatory mites, and optionally one or more components selected from a nutritional source for said mites, a carrier, an oviposition substrate, and a hydrophilic material, for controlling a pest. Indeed, the compositions or devices described herein and the predatory mites obtainable by the rearing method described herein can be used for the biological control of pests including but not limited to plant pests such as *thrips* and spider mites. In particular embodiments, the pest comprises *thrips* and/or (spider) mites. In certain embodiments, the crop pest comprises *thrips*. Exemplary *thrips* species include Western Flower *Thrips* (*Frankliniella occidentalis*) and Onion *thrips* (*Thrips tabaci*). Exemplary mites include two-spotted spider mites (*Tetrancychus urticae*), red mites (*Dermanyssus gaffinae*), cured ham mites (*Tyrophagus putrescentiae*) and dust mites (*Dermatophagoides farinae* and *Dermatophagoides pteronyssinus*). Thus the methods provided herein facilitate rearing of predator mites for use in control of each or all of these mites.

The compositions, devices and/or predatory mites may thus be used for protecting any crop, organism or item for which biological control of pests, more particularly mites is desired. Exemplary crops include vegetable crops such as peppers, eggplants, cucumbers, melons, watermelons, grapes, strawberries, raspberries, ornamental crops (e.g. roses), or tree crops (e.g. apple trees, *Citrus* spp.). Exemplary organisms include, but are not limited to poultry, cured meat. Exemplary items include, but are not limited to fabrics, for example carpets.

Further provided herein is the use of succulent plants for the rearing of mites such as predatory mites, more particularly the use of succulent plants in combination with plant pollen (obtained from other plants than said succulents) for the rearing of mites such as predatory mites.

The following examples are provided for the purpose of illustrating the present invention and by no means are meant and in no way should be interpreted to limit the scope of the present invention.

EXAMPLES

1) Rearing of *Euseius stipulatus*

A series of rearing experiments was conducted to evaluate the suitability of a variety of succulent plants for the rearing of *Euseius stipulatus* mites.

The rearing experiments were conducted in plastic boxes having a ventilation lid. 17 g of saw dust was placed into each box as a carrier. Loose cotton fibers were placed on top of the saw dust as oviposition substrates. Succulent plant material was placed on top of the saw dust and fibers. The following succulents, representing four different genera, were included in the test: *Crassula hobbit*; *Crassula* sp.; *Crassula ovata*; *Sempervivum* sp.; *Huernia* sp.; and *Kalanchoe thyrsiflora*. The quantity of plant material was chosen so as to provide comparable plant surface area for all plant treatments at approximately 25 cm². The succulent plant material was not replaced during the experiment. A control experiment was conducted without succulent plant material At the beginning of the experiments, each box was inoculated with 200 mites (*Euseius stipulatus*). Subsequently, the boxes were placed in a climate chamber at a temperature of about 22.5° C. and a relative humidity of about 70%.

0.1 g of cattail (*Typha*) pollen was introduced once per week in each box as a nutritional source for the predatory mites.

After 14 days, the number of mites in each box were counted. The results are summarized in Table 1. The results show that predatory mites such as *Euseius stipulatus* can be successfully reared on a range of succulent plant species from different genera, although the yield may differ between plant species. It is further clear that the presence of plant material is essential, as no reproduction/survival was seen in the control treatment without the plant. Moreover, the method had the advantage that the plant material did not need to be replaced during the entire experiment.

TABLE 1

| Number of mites obtained after 14 days | |
| --- | --- |
| Plant species | Number of mites |
| *Crassula hobbit* | 561 |
| *Crassula* sp. | 1139 |
| *Crassula ovata* | 680 |
| *Sempervivum* sp. | 765 |
| *Huernia* sp. | 272 |
| *Kalanchoe thyrsiflora* | 399 |
| Control | 0 |

2) Rearing of *Amblyseius swirskii*

A series of rearing experiments was conducted to evaluate the suitability of a variety of succulent plants for the rearing of *Amblyseius swirskii* mites.

The rearing experiments were conducted in plastic boxes having a ventilation lid. 17 g of saw dust was placed into each box as a carrier. Loose cotton fibers were placed on top of the saw dust as oviposition substrates. Succulent plant material was placed on top of the saw dust and fibers. The following succulents, representing four different genera, were included in the test: *Crassula hobbit*; *Crassula* sp.; *Crassula ovata*; *Sempervivum* sp.; *Huernia* sp.; and *Kalanchoe thyrsiflora*. The quantity of plant material was chosen so as to provide comparable plant surface area for all plant treatments at approximately 25 cm². The succulent plant material was not replaced during the experiment. A control experiment was conducted without succulent plant material.

At the beginning of the experiments, each box was inoculated with 50 *Amblyseius swirskii* mites. Subsequently, the boxes were placed in a climate chamber at a temperature of about 22.5° C. and a relative humidity of about 70%.

Cattail (*Typha*) pollen were introduced three times per week (ad libitum) in each box as a nutritional source for the predatory mites.

The number of mites in each box was counted after 2, 3, 4, 5, and 6 weeks. The results are summarized in Table 2. No surviving mites were counted in the control experiment after two weeks. Generally, an initial decrease of the mite population was observed in the other experiments, followed by a strong increase of the population. The results show that predatory mites such as *Amblyseius swirskii* can be successfully reared on a range of succulent plant species from different genera.

TABLE 2

Number of mites obtained after 2, 3, 4, 5, and 6 weeks

| Succulent | 2 weeks | 3 weeks | 4 weeks | 5 weeks | 6 weeks |
| --- | --- | --- | --- | --- | --- |
| *Huernia* sp. | 34 | 140 | 269 | 405 | 725 |
| *Crassula hobbit* | 37 | 226 | 400 | 521 | 659 |
| *Crassula ovata* | 36 | 214 | 376 | 674 | 803 |
| *Kalanchoe thyrsiflora* | 44 | 179 | 115 | 190 | 260 |
| *Crassula* sp. | 57 | 225 | 312 | 409 | 544 |
| *Sempervivum* sp. | 32 | 137 | 408 | 525 | 692 |
| Control | 0 | 0 | 0 | 0 | 0 |

The invention claimed is:

1. A method for rearing, storing, or shipping predatory mites comprising contacting a population of said predatory mites with a succulent plant during said rearing, storing or shipping.

2. The method according to claim 1, further comprising contacting said population of predatory mites with a nutritional source for said predatory mites; and allowing said population to feed on said nutritional source.

3. The method according to claim 2, wherein said nutritional source comprises plant pollen.

4. The method according to claim 3, wherein said pollen are obtained from one or more plant species other than said succulent plant.

5. The method according to claim 1, wherein said predatory mites comprise members of the family Phytoseiidae.

6. The method according to claim 1, wherein said predatory mites are from a genus selected from the group consisting of *Euseius, Amblyseius, Neoseiulus, Iphiseius, Indoseiulus, Kampimodromus, Typhlodromalus, Phytoseius* and *Typhlodromus*.

7. The method according to claim 1, wherein said succulent plant is a member of a family selected from the list consisting of Crassulaceae, Cactaceae, and Apocynaceae.

8. The method according to claim 1, comprising contacting said predatory mites with one or more succulent plant leaves.

9. The method according claim 1, which comprises maintaining said population of predatory mites at 20 to 30° C. and 65 to 90% relative humidity.

10. The method according to claim 1, further comprising cultivating said population of predatory mites in the presence of an oviposition substrate other than said succulent plant.

11. The method according to claim 10, wherein said oviposition substrate is selected from the group consisting of a fiber, a thread, a fibrous material and an open cell foam material.

12. The method according to claim 1, wherein said predatory mites are contacted with a non-reproductive part of said succulent plant.

13. An isolated composition comprising a succulent plant or one or more parts thereof, a population of predatory mites and a nutritional source for mites.

14. The composition according to claim 13, further comprising an oviposition substrate for said predatory mites.

15. The composition according to claim 14, wherein said oviposition substrate is selected from the group consisting of a fiber, a thread, a fibrous material and an open cell foam material.

16. The composition according to claim 13, wherein said nutritional source comprises plant pollen.

17. The composition according to claim 13, further comprising a carrier material.

18. A predatory mite population obtainable by the method for rearing predatory mites according to claim 1.

* * * * *